(12) United States Patent
Aizawa et al.

(10) Patent No.: US 9,115,381 B2
(45) Date of Patent: Aug. 25, 2015

(54) METHOD OF INCREASING THE PRODUCTIVITY OF EUCARYOTIC CELLS IN THE PRODUCTION OF RECOMBINANT FVIII

(75) Inventors: Peter Aizawa, Johannesshov (SE); Irene Agerkvist, Danderyd (SE)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 14/113,923

(22) PCT Filed: May 14, 2012

(86) PCT No.: PCT/EP2012/058899
§ 371 (c)(1),
(2), (4) Date: Oct. 25, 2013

(87) PCT Pub. No.: WO2012/156356
PCT Pub. Date: Nov. 22, 2012

(65) Prior Publication Data
US 2014/0051123 A1 Feb. 20, 2014

Related U.S. Application Data

(60) Provisional application No. 61/489,406, filed on May 24, 2011.

(30) Foreign Application Priority Data

May 13, 2011 (EP) .................................. 11166071

(51) Int. Cl.
| | |
|---|---|
| C12P 21/00 | (2006.01) |
| C07K 14/755 | (2006.01) |
| C12N 5/00 | (2006.01) |
| C12N 5/071 | (2010.01) |

(52) U.S. Cl.
CPC ............. *C12P 21/005* (2013.01); *C07K 14/755* (2013.01); *C12N 5/0018* (2013.01); *C12N 5/0686* (2013.01); *C12N 2510/02* (2013.01); *C12N 2511/00* (2013.01); *C12N 2521/00* (2013.01); *C12N 2527/00* (2013.01)

(58) Field of Classification Search
None
See application file for complete search history.

(56) References Cited

U.S. PATENT DOCUMENTS

2008/0131934 A1 6/2008 Crowley et al.
2008/0227691 A1* 9/2008 Ostergaard et al. ................ 514/8

FOREIGN PATENT DOCUMENTS

WO 2006/103258 10/2006
WO 2008/006494 1/2008

OTHER PUBLICATIONS

Chun et al., "Enhanced production of recombinant B-domain deleted factor VIII from Chinese hamster ovary cells by propionic and butyric acids", Biotechnology Letters 25: 315-319, 2003.*
Ham's F-12 Nutrient Mix Formulation—Life Technologies. Retrieved from < http://www.lifetechnologies.com/us/en/home/technical-resources/media-formulation.64.html > on Oct. 22, 2014.*
Caldwell, J.J.S., "New Developmetns in Hollow-Fiber Cell Culture", Reprinted from American Biotechnology Laboratory, Jul. 2004, pp. 1-6. Retrieved from < http://www.fibercellsystems.com/documents/article-newdevelopments-cadwell.pdf >.*
Zhang et al. "Engineering Considerations for Process Development in Mammalian Cell Cultivation." Current Pharamaceutical Biotechnology, vol. 11, No. 1, Jan. 2010, pp. 103-112.
Barrett et al. "Microwell Engineering Characterization for Mammalian Cell Culture Process Development." Biotechnology and Bioengineering, vol, 105, No. 2, Feb. 1, 2010, pp. 260-275.
Whitford et al. "Interest in Hollow-Fiber Perfusion Bioreactors is Growing." Bioprocess International, vol. 7, No. 9, Oct. 2009. pp. 54-64.
Kolind et al. "Optimisation of the Factor VIII yield in mammalian cell cultures by reducing the membrane bound fraction." Journal of Biotechnology, vol. 151, No. 4, Feb. 20, 2011, pp. 357-362.
Swiech et al. "Transient transfection of serum-free suspension HEK 293 cell culture for efficient production of human rFVIII." BMC Biotechnology, vol. 11, No. 114, 2001, pp. 1-10.
Keane et al. "Effect of Shear Stress on Expression of a Recombinant Protein by Chinese Hamster Ovary Cells." Biotechnology and Bioengineering, 81:211-220, 2003.
Godoy-Silva et al. "Physiological Responses of CHO Cells to Repetitive Hydrodynamic Stress." Biotechnology and Bioengineering, vol. 102, No. 6, Aug. 15, 2009.
Frangos et al. "Shear Stress Induced Stimulation of Mammalian Cell Metabolism." Biotechnolgoy and Bioengineering, vol. 32, pp. 1053-1060, 1988.
Giard et al. "Human Interferon Production with Diploid Fibroblast Cells Grown on Microcarriers." Biotechnology and Bioengineering, vol. 21, pp. 433-442, 1979.
Tanzeglock et al. "Induction of Mammalian Cell Death by Simple Shear and Extensional Flows." Biotechnology and Bioengineering, vol. 104, No. 2, Oct. 1, 2009, pp. 360-370.

* cited by examiner

*Primary Examiner* — Suzanne M Noakes
(74) *Attorney, Agent, or Firm* — Jacobson Holman PLLC

(57) ABSTRACT

A method of increasing productivity, in particularly cell-specific productivity, of recombinant factor VIII (rFVIII) produced in a eukaryotic cell suspension during culturing of the eucaryotic cell suspension in a culturing medium containing not more than 500 μM $CaCl_2$, at least a non-ionic detergent and other nutrient components needed for the cells to grow and produce rFVIII, the cell suspension is cultured under conditions inducing a shear stress mechanically to the eucaryotic cell suspension by adding a power density of at least 3 $W/m^3$.

17 Claims, 3 Drawing Sheets

METHOD OF INCREASING THE PRODUCTIVITY OF EUCARYOTIC CELLS IN THE PRODUCTION OF RECOMBINANT FVIII

This is a 371 of PCT/EP12/058899 filed May 14, 2012, which has a priority of Europe no. 11166071.8, filed May 13, 2011, U.S. provisional application No. 61/489,409, filed May 24, 2011, hereby incorporated by reference.

The present invention pertains to a method of increasing yield of recombinant human factor VIII (rFVIII) during cell cultivation.

BACKGROUND OF THE INVENTION

1. Field of the Invention

The present invention provides methods of increasing yield in the protein production by cultured cells, especially mammalian cells. Specifically, the present invention relates to methods of preparing protein product(s), e.g., a glycoprotein product(s), wherein the protein product characteristics are controlled by manipulating the cell culture environment to increase stress applied to the cells.

2. Related Background Art

A large proportion of biotechnology products, whether commercially available or in development, are protein therapeutics. There is a large and increasing demand for production of proteins in mammalian cell cultures and for improved methods related to such production. Such improved methods are needed especially when large glyco-proteins with low cellular expression levels are produced. One such protein, FVIII, has an expression level at least two to three orders lower than other recombinant proteins produced in mammalian cells. A common problem encountered in late-phase development of large-scale therapeutic protein production is increasing demand due to larger clinical trials and contaminations in the cell culture production plant which decrease capacity. To meet the increased demand the total production level can be increased by several ways. However, most of them such as finding a better cell clone or improving the culture medium are very tedious tasks and therefore not often quick enough options. Other ways to increase the productivity is to increase the production scale or increase the density of cells in fed-batch or perfusion mode culture. Also these process changes are accompanied with large investment costs and for the case of high density cultures oxygen limitation in the culture tank will generally set a limit for the maximum cell density that can be used for production. Therefore, there is a need in art for new methods of increasing productivity.

Keane J. T. et al. Effect of shear stress on expression of a recombinant proetine by chinese hamster ovary cells; Biotechnology and Bioengineering, 81:211-220, 2003, subjected attached CHO cells to shear force for 32 h and monitored recombinant human growth hormone production and glucose metabolism. They observed that when shear force was increased from 0.005 N/m$^2$ (0.02 W/m$^3$) to 0.80 N/m$^2$ (6.4×10$^2$ W/m$^3$), recombinant protein production rate was reduced by 51%, glucose uptake rate was increased by 42%, and lactate production was decreased by 50%.

Godoy-Silva R et al. Physiological responses of CHO cells to repetitive hydrodynamic stress; Biotechnology and Bioengineering, Vol. 103, No. 6, Aug. 15, 2009, examined the effect of repetitive hydrodynamic stress on CHO cells and came to the conclusion that energy dissipation rate up to 6.4×10$^6$ W/m$^3$ did not affect cell growth, death, and productivity.

J. A. Frangos et al. Shear stress induced stimulation of mammalian cell metabolism; Biotechnology and Bioengineering, Vol. 32, Pp. 1053-1060(1988) discloses a flow apparatus for the study of the metabolic response of anchorage-dependent cells to a wide range of steady and pulsatile shear stresses under well-controlled conditions. The data demonstrate that physiological levels of steady shear stress and the onset of shear stress dramatically stimulate prostacyclin production in cultured human endothelial cells.

Giard and co-workers observed that human fibroblasts secrete up to 30-fold greater amounts of interferon when maintained on microcarrier in spinner flasks compared to cells in roller bottles (D. J. Giard, D. H. Loeb, W. G. Thilly, D. 1. C. Wang, and D. W. Levine, Biotechnol. Bioeng., 21, 433(1979)). Since the shear stresses that cells are exposed to in the spinner flasks are much higher than those in roller bottles, the increased production may be attributable to shear-induced stimulation of interferon synthesis.

Timm Tanzeglock et al, Induction of mammalian cell death by simple shear and extensional flows; Biotechnology and Bioengineering, Vol. 104, No. 2, Oct. 1, 2009 discloses whether the type of shear flow, to which cells are exposed, influences the initiation of cell death. It is shown that mammalian cells, indeed, distinguish between discrete types of flow and respond differently. Two flow devices were employed to impose accurate hydrodynamic flow fields: uniform steady simple shear flow and oscillating extensional flow. To distinguish between necrotic and apoptotic cell death, fluorescensce activated cell sorting and the release of DNA in the culture supernatant was used. Results show that chinese hamster ovaries and human embryonic kidney cells will enter the apoptotic pathway when subjected to low levels of hydrodynamic stress (around 2 Pa) in oscillating, extensional flow. In contrast, necrotic death prevails when the cells are exposed to hydrodynamic stresses around 1 Pa in simple shear flow or around 500 Pa in extensional flow. These threshold values at which cells enter the respective death pathway should be avoided when culturing cells for recombinant protein production to enhance culture longevity and productivity.

WO 2006/103258A1 discloses a method for increasing the yield of a protein produced by cultivating eukaryotic cells and adding an ionic substance to the culture medium prior to harvest of the protein. Suitable ionic substances are the salts of the Hofmeister series and amino acids.

WO 2008/006494A1 discloses a process for the culturing of cells, preferably E1-immortalized HER cells, more preferably PER.C6 cells in a reactor in suspension in a cell culture medium, wherein the cells produce a biological substance, preferably an antibody, wherein at least one cell culture medium component is fed to the cell culture and wherein the cell culture comprising the cells, the biological substance and cell culture medium is circulated over a separation system and wherein the separation system separates the biological substance from substances having a lower molecular weight than the biological substance and wherein the biological substance is retained in or fed back into the reactor. Preferably part of the substances of lower molecular weight is continuously removed from the cell culture.

Zhang, Hu et al report in Current Pharmaceutical Biotechnology, Volume 11, Number 1, January 2010, pp. 103-112 (10) that mammalian cell cultivation plays a great role in producing protein therapeutics in the last decades. Many engineering parameters are considered for optimization during process development in mammalian cell cultivation, only shear and mixing are especially highlighted in this paper. It is believed that shear stress due to agitation has been overestimated to damage cells, but shear may result in nonlethal physiological responses. There is no cell damage in the regions where bubbles form, break up and coalescence, but shear stress becomes significant in the wake of rising bubbles and causes great damage to cells in bubble burst regions. Mixing is not sufficient to provide homogeneous dissolved oxygen tension, pH, $CO_2$ and nutrients in large-scale bioreactors, which can bring severe problems for cell growth, product formation and process control. Scale-down reactors have been developed to address mixing and shear problems for parallel operations. Engineering characterization in conventional and recently developed scale-down bioreactors has been briefly introduced. Process challenges for cultivation of industrial cell lines in high cell densities as well as cultivation of stem cells and other human cells for regenerative medicine, tissue engineering and gene therapy are prospected. Important techniques, such as micromanipulation and nanomanipulation (optical tweezers) for single cell analysis, computational fluid dynamics (CFD) for shear and mixing characterization, and miniaturized bioreactors, are being developed to address those challenges.

Timothy A. Barrett et al. in Biotechnology and Bioengineering, Vol. 105, No. 2, pages 260-275 report about experimentation in shaken microplate formats offering a potential platform technology for the rapid evaluation and optimization of cell culture conditions. There is described a detailed engineering characterization of liquid mixing and gas-liquid mass transfer in microwell systems and their impact on suspension cell cultures.

Provided that cell growth and antibody production kinetics are comparable to those found in currently used shake flask systems then the microwell approach offers the possibility to obtain early process design data more cost effectively and with reduced material requirements. This work describes a detailed engineering characterization of liquid mixing and gas-liquid mass transfer in microwell systems and their impact on suspension cell cultures. For growth of murine hybridomas cells productizing IgGl, 24-well plates have been characterized in terms of energy dissipation (P/V) (via Computational Fluid Dynamics, CFD), fluid flow, mixing and oxygen transfer rate as a function of shaking frequency and liquid fill volume. Predicted $k_La$ values varied between 1.3 and 29 $h^{-1}$; liquid-phase mixing time, quantified using iodine decolorization experiments, varied from 1.7 s to 3.5 h; while the predicted P/V ranged from 5 to 35 W $m^{-3}$. CFD simulations of the shear rate predicted hydrodynamic forces will not be detrimental to cells. For hybridomas cultures however, high shaking speeds (>250 rpm) were shown to have a negative impact on cell growth, while a combination of low shaking speed and high well fill volume (120 rpm; 2,000 µL) resulted in oxygen limited conditions. Based on these findings a first engineering comparison of cell culture kinetics in microwell and shake flask formats was made at matched average energy dissipation rates. Cell growth kinetics and antibody titer were found to be similar in 24-well microtiter plates and 250 mL shake flasks. Overall this work has demonstrated that cell culture performed in shaken microwell plates can provide data that is both reproducible and comparable to currently used shake flask systems while offering at least a 30-fold decrease in scale of operation and material requirements. Linked with automation this provides a route towards the high through-put evaluation of robust cell lines under realistic suspension culture conditions.

William G. Whitford and John S. Cadwell in BioProcess International 2009, Vol. 7, No. 9, pages 54-64 report about growing interest in hollow-fiber perfusion bioreactors.

SUMMARY OF THE INVENTION

An object of the present invention was to provide a method of increasing the productivity, in particular cell-specific productivity, of recombinant factor VIII (rFVIII), in particular human rFVIII produced in an eukaryotic cell suspension during culturing of said eukaryotic cell suspension in a culturing medium containing not more than 500 µM $CaCl_2$, at least a non-ionic detergent and other nutrient components needed for the cells to grow and produce rFVIII, characterized in that said cell suspension is cultured under conditions inducing a shear stress by mechanical means to the eukaryotic cell suspension. The shear stress is achieved by adding an input of power density of more than 3 $W/m^3$ to the cell suspension. The conditions inducing a shear stress are events which induce mechanical movements of the cell suspension or the cells in the suspension. Typically, the shear stress is applied directly to the cultured cells. The mechanical means are in particular those which are able to stir the cell culture suspension.

Although the effects of the present invention have been investigated with HEK293 these cells are typical human cells and the skilled person expects that the results obtained with HEK293 cells will also be achieved with other cells of human cell lines.

The power input (power density which is an equivalent term of energy dissipation rate, $\epsilon$) introduced by the mechanical means is calculated according to the following formula: $\epsilon = Np \cdot n^3 \cdot di^5)/V$ where Np is the turbulent power number for the impeller, n is the stirring rate measured as impeller revolutions per second, di is the impeller diameter measured in meter and V is the culture volume in cubic meters. The power added to the cell suspension to introduce shear stress should not exceed a value where the cells are destroyed, typically a maximum value corresponding to 2000 $W/m^3$ should not be exceeded. In particular, the power density added to the cell suspension to introduce shear stress is in the range of from of from 3 $W/m^3$ to 2000 $W/m^3$, preferably 15 $W/m^3$ to 1500 $W/m^3$, more preferably 30 $W/m^3$ to 1250 $W/m^3$, still more preferably 50 $W/m^3$ to 1000 $W/m^3$.

In one embodiment of the invention, the power is introduced by a mechanical movement of the cell suspension. In a further embodiment of the invention the mechanical movement of the cell suspension is performed by means of pumping the cell suspension through a tangential filtration membrane such as a hollow fiber membrane or the mechanical movement of the cell suspension is performed by means of a rotating element such as a stirrer, propeller or impeller.

In particular, the rFVIII is a B-domain deleted rFVIII, in particular a human B-domain deleted FVIII.

In yet another embodiment of the invention the eukaryotic cells are HEK293 cells. The rFVIII molecule is in particular produced in and accumulated on the surface of the HEK293 cells. For isolating rFVIII it may be advantageous to employ conditions for releasing the rFVIII from the cell surfaces e.g. by increasing the ionic strength of the medium surrounding the cells or other means for weakening the attraction forces of rFVIII and HEK293 cell surfaces.

In still a further embodiment of the invention the non-ionic detergents are selected from Pluronic-F68, Tween 20 and Tween 80. Typically, the non-ionic detergents have a concentration of 0.00001 wt % to 1 wt %, in particular 0.0001 wt % to 0.1 wt %, most suitable 0.001 wt % to 0.01 wt %.

In another embodiment of the process of the invention, a low $CaCl_2$ concentration in the culture medium is adjusted for controlling cell aggregation for example for minimizing cell aggregation.

According to the invention the power may be introduced into the cell cultivation by virtue of a mechanical movement of the cell suspension. The mechanical movement of the cell suspension can for example be performed by means of a stirrer or a respective mechanical analogue such as a shaking device.

In a particular embodiment of the invention the power density input e.g. due to mechanical originating movement of the cell suspension is initiated by an impeller equipped culturing container or a culturing container such as for an example a a disposable Wave® cultivation bag without impeller or similar instead moving the bag in the gravity from planet earth (with for example a rocking machine), thus inducing shear stress in said cell suspension container or the shear stress in the cell suspension container is induced by pumping the cell suspension through a static mixer or a filter device.

DETAILED DESCRIPTION OF THE INVENTION

In the method of the invention higher mechanical energy by introducing higher power is applied to the culturing vessel containing the eukaryotic cell suspension that grows and produces rFVIII compared to conventional processes. The amount of power can be determined in terms of energy dissipation although other parameters can be correlated to power input. The invention is based on the result of an unusually high FVIII productivity when cells are stirred at high stirring rates in a shaker bottle or stirred tank bioreactor.

According to the invention any eukaryotic cell or cell-line can be used, in particular the eukaryotic cells are HEK293 cells. The genetically manipulated cells produce rFVIII in particular a B-domain deleted rFVIII as e.g. disclosed in WO-A-2001/070968 and WO-A-2007/003582.

The combination of the manufacturing of the rFVIII molecule in HEK293 cells is a particular embodiment of the method of the invention and explained further in the examples hereinbelow.

In the method of the invention it has been shown that the rFVIII molecule produced in HEK293 cells are associated with the cells and adhere to the cell surface after being produced inside the cells, as further described in WO-A-2006/103258, Kohlind 2010 (Kohlind et. al., The B-domain of Factor VIII reduces cell membrane attachment to host cells under serum free conditions. Journal of Biotechnology, 147 (2010), 198-204.) and Kohlind 2011 (Kohlind et. al., Optimisation of the Factor VIII yield in mammalian cell cultures by reducing the membrane bound fraction. Journal of Biotechnology, 151 (2011), 357-362).

In the method of the invention the culturing medium for growing of the cells and producing the rFVIII contains non-ionic detergents. Typically a polyoxyethylene derivative of sorbitan monolaurate such as Tween® which is a family of many products distinguished by the length of the polyoxyethylene chain and the fatty acid ester moiety. Another useful non-ionic detergent are Poloxamers which are nonionic tri-block copolymers composed of a central hydrophobic chain of polyoxypropylene (poly(propylene oxide)) flanked by two hydrophilic chains of polyoxyethylene (poly(ethylene oxide)). Poloxamers are also known by the trade name Pluronics®. The non-ionic detergents may be selected from Pluronic-F68, Tween 20 and Tween 80, in particular in a concentration of 0.00001 wt % to 1 wt %, or 0.0001 wt % to 0.1 wt %, or 0.001 wt % to 0.01 wt %.

Figure 1:
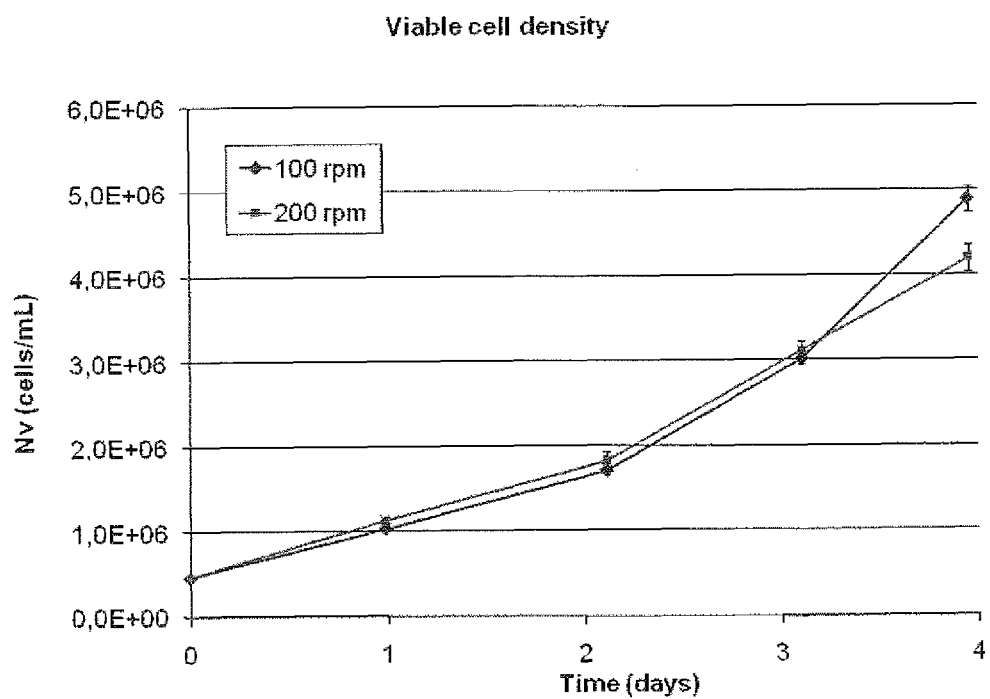
FIG. 1: Viable cell density profiles.
Figure 2:
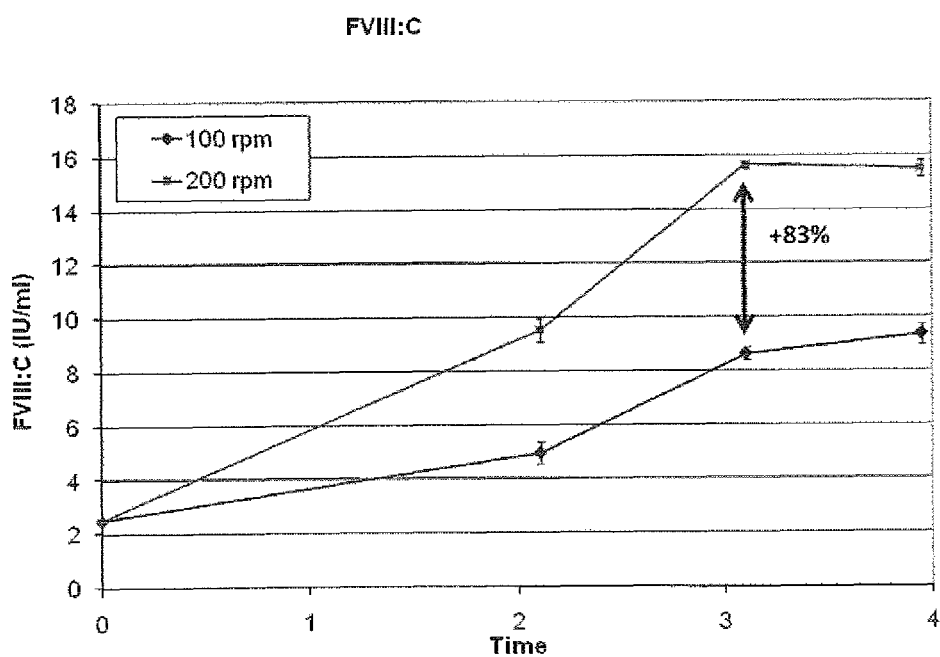
FIG. 2: Accumulated FVIII:C profiles.

The following describes the method of the invention in more detail. Cells were cultivated at different shaker frequencies in 125 mL baffled E-bottles. While cell growth profiles were similar in the low stirring and high stirring cultures (FIG. 1) accumulated productivity was surprisingly 83% higher in the high stirring cultures after 3 days of batch cultivation (FIG. 2).

Another embodiment of the invention was performed in batch mode cultures in parallel controlled stirred tank bioreactors. The culture which has been exposed to higher mechanical stress showed higher productivity compared to low stirring cultures. This showed that while other culture parameters such as pH, DOT (dissolve oxygen tension) and temperature are kept constant the higher stirring is causing the increased productivity.

In yet another embodiment the invention was examined experimentally in a perfusion mode culture in a 2 L stirred tank bioreactor. The culture was run at steady-state perfusion mode with exponentially growing cells kept at the desired cell density by bleeding off cells from the reactor in a rate that kept the cell density in the reactor constant. While other culture parameters were kept constant, the higher stirring rate increased cell specific productivity.

In yet another embodiment the invention was examined experimentally in a 100 L production-scale bioreactor which was run in perfusion mode to achieve higher cell densities. The experiment confirms that increased productivity can be achieved also in large-scale cultures by increasing the shear forces and energy input by increased stirring.

In yet another embodiment the invention was examined experimentally in a 2 L stirred tank bioreactor which was run in perfusion mode with either a continuous centrifuge or a hollow fiber unit run with an alternating tangential flow (ATF). Surprisingly it was showed that the increased shear which is added to the culture by the ATF unit also increases FVIII productivity.

EXAMPLES

Example 1

Exponentially growing HEK293F cells producing BDDrFVIII were centrifuged and thereafter the cell pellet was resuspended in serum free cell culture medium to a viable cell density of $0.5 \times 10^6$ cells/mL. Cells were thereafter cultivated in 125 mL baffled Erlenmeyer bottles at 100 rpm or 200 rpm in shaker incubators in a 5%/95% $CO_2$/air overlay at 37° C. Cell density was measured in all cultures each day by the trypan blue exclusion method with the automatic Cedex (Innovatis) cell counter. Accumulated FVIII was released from the cells by increasing the ionic concentration in the cell suspension to 1 M NaCl+30 mM $CaCl_2$. The cells were removed by centrifugation and FVIII was determined by the Chromogenic substrate method (Coatest® SP FVIII). Growth profiles were similar (FIG. 1) while the high stirring cultures showed 83% higher accumulated FVIII:C concentration after 3 days of batch culture (FIG. 2).

Example 2

HEK293F cells producing BDDrFVIII were cultivated in parallel in batch mode at different stirring rates in an equipment with six 0.4 L bioreactors (Multifors, Infors). The aim was to examine how stirring rate affects productivity in a controlled environment where the other cell culture parameters are kept constant. To be able to examine high stirring rates (>300 rpm) the bioreactor electric stirrer motors, normally used for cell culture applications, were exchanged to more powerful stirrer motors, normally used for bacterial culture applications, which could run up to 1200 rpm. Dissolved oxygen tension (DOT) set-point was set to 90% and regulated with air addition from a sparger stone in the cell suspension. Viable cell density, viability and aggregate rate were measured by Cedex (Innovatis) cell counter. Accumulated FVIII was released from the cells by increasing the ionic concentration in the cell suspension to 1 M NaCl+30 mM $CaCl_2$. The cells were removed by centrifugation and FVIII was determined by the Chromogenic substrate method (Coatest® SP FVIII). The examined stirring rates, energy dissipation which is an equivalent term to power density as used herein ($\epsilon$) rate and cell specific productivity (qp) are shown in table 1. Increased stirring rate between 200 up to 950 rpm showed increased cell specific productivity The productivity increase leveled off above 950 rpm as seen by a lower qp at 1200 rpm compared to 950 rpm.

TABLE 1

| Stirring rate [rpm] | $\epsilon$ [W/m$^3$] | qp [IU/1E6 cells/day] |
| --- | --- | --- |
| 200 | 3 | 0.83 |
| 450 | 33 | 1.27 |
| 700 | 125 | 1.9 |
| 950 | 267 | 2.45 |
| 1200 | 632 | 2.14 |

Example 3

Figure 3:
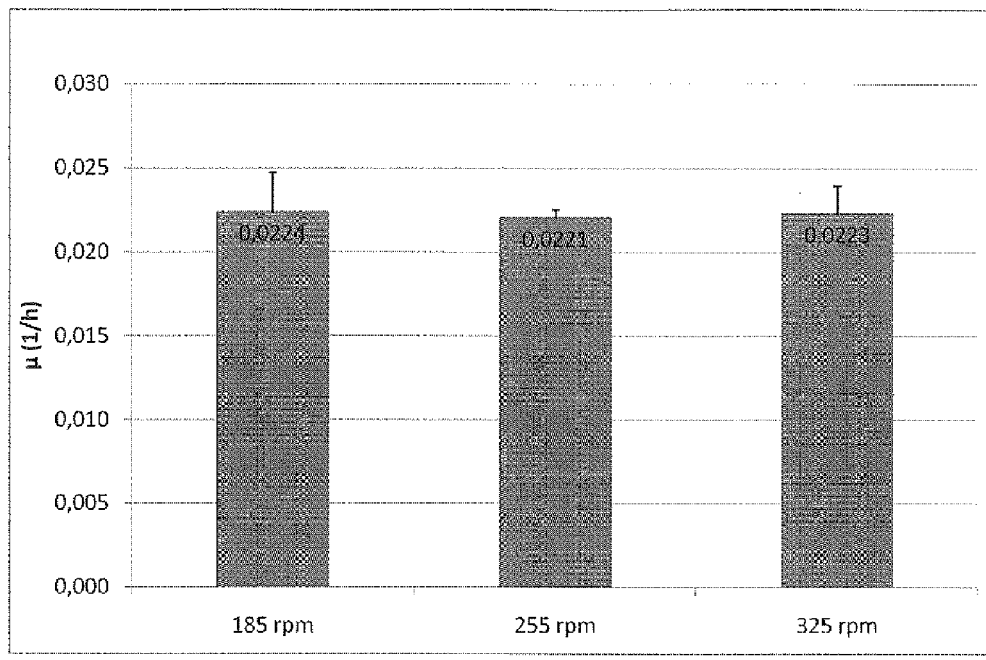
FIG. 3: Cell specific growth rate.
Figure 4:
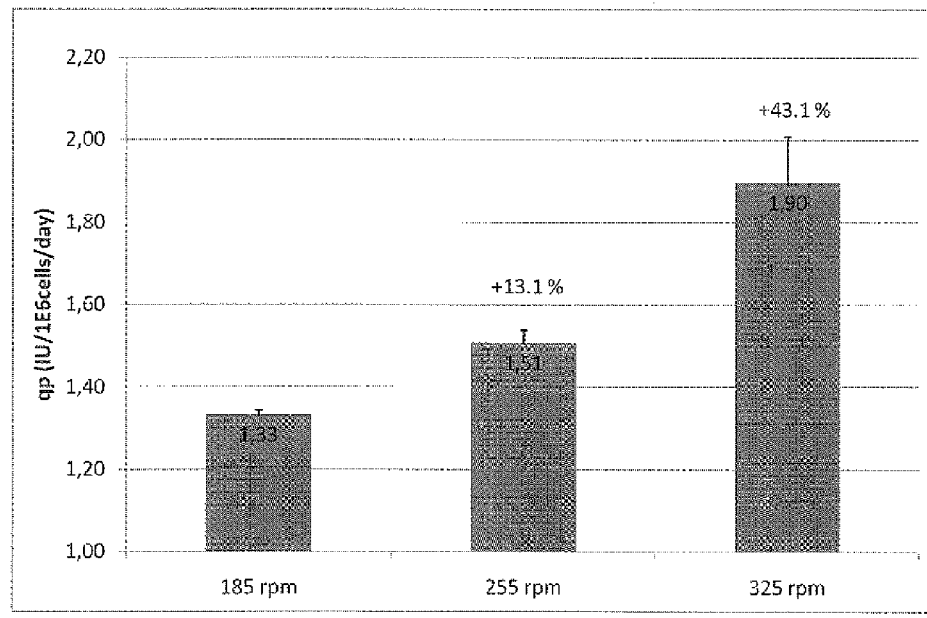
FIG. 4: Cell specific productivity in continuous culture run at different stirring rates.

HEK293F cells producing BDDrFVIII were cultivated in a continuous steady-state perfusion culture in a 2 L stirred tank bioreactor. The bioreactor uses a 90 mm pitched blade impeller to achieve stirring. Medium exchange was achieved by using a hollow fiber filter which also create shear to the cell suspension. All cell culture parameters except for the stirring rate were kept constant during the experiment. Viable cell density, viability and aggregate rate were measured by Cedex (Innovatis) cell counter. Accumulated FVIII was released from the cells by increasing the ionic concentration in the cell suspension to 1 M NaCl+30 mM $CaCl_2$. The cells were removed by centrifugation and FVIII was determined by the Chromogenic substrate method (Coatest® SP FVIII). The examined stirring rates were 185; 255 and 325 rpm which adds 113, 210 and 610 W/m$^3$ of power to the culture, respectively. Stirring rate did not affect the cell specific growth rate (FIG. 3). However, increased stirring rate increased the cell specific productivity (FIG. 4).

Example 4

HEK293F cells producing BDDrFVIII were cultivated in 15 different 100 L production-scale stirred tank bioreactor batches, two of them using a low energy dissipation rate (6 W/m$^3$) as control and 13 with a high energy dissipation rate (29 W/m$^3$) to study effect of increased shear forces. The mean value of cell density was 29.2 10$^6$ cells/ml in the two low energy batches and 27.6 10$^6$ cells/ml in the 13 high energy batches. The bioreactor uses a 225 mm pitched blade impeller to achieve stirring. Medium exchange was achieved by using a continuous centrifuge. Viable cell density and viability were measured by Cedex (Innovatis) cell counter. Accumulated FVIII was released from the cells by increasing the ionic concentration in the cell suspension to 0.3 M NaCl+30 mM $CaCl_2$. The cells were removed by centrifugation and FVIII was determined by the Chromogenic substrate method (Coatest® SP FVIII). The examined stirring rates were 45 and 75 rpm which adds 6 and 29 W/m$^3$ of energy to the culture, respectively. The experiment showed that increasing the energy input (energy dissipation rate, $\epsilon$) to the culture by increasing the stirring rate increased productivity (Table 2). In conclusion it was possible to achieve increase productivity by increasing shear forces also in large-scale production cultures in the same way as seen in small-scale cultures.

TABLE 2

| Stirring rate [rpm] | $\epsilon$ [W/m$^3$] | Accumulated FVIII:C Mean value [IU/mL] |
| --- | --- | --- |
| 45 | 6 | 45 (n = 2) |
| 75 | 29 | 59 (n = 13) |

Example 5

Figure 5:
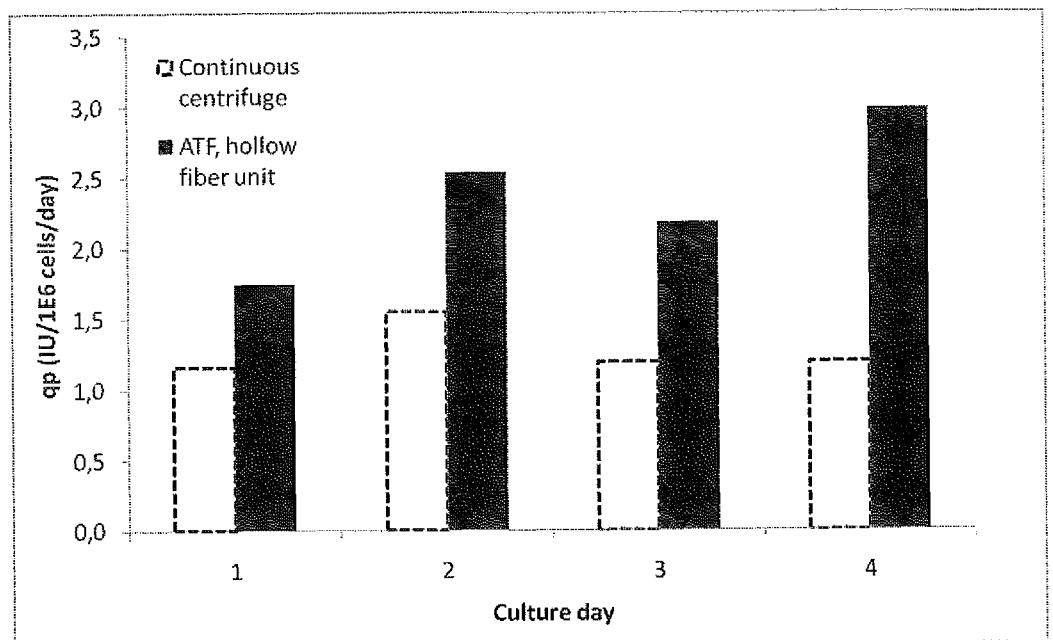
FIG. 5: Cell specific productivity in continuous culture comparing continuous centrifuge with ATF hollow fiber device.

HEK293F cells producing BDDrFVIII were cultivated in perfusion mode in a 2 L stirred tank bioreactors stirred constantly at 185 rpm with a 90 mm, 45° pitched blade impeller. The normal mode of operation for the bioreactor was to use a continuous centrifuge to achieve medium exchange by perfusion. As a comparison a hollow fiber unit was used to achieve perfusion by medium exchange. The hollow fiber unit was run by alternating tangential flow which means that cells are pumped in and out to the filter membrane which continuously adds shear forces to the cell culture. The other cell culture parameters such as stirring rate, pH, dissolved oxygen tension and temperature were kept constant at the same values in both cultures. Surprisingly it was discovered that if shear forces are increased by increased energy input to the culture by using a hollow fiber membrane to achieve shear forces the cell specific FVIII production rate can be increased significantly (FIG. 5). Accumulated FVIII was released from the cells by increasing the ionic concentration in the cell suspension to 1 M NaCl+30 mM $CaCl_2$. The cells were removed by centrifugation and FVIII was determined by the Chromogenic substrate method (Coatest® SP FVIII).

The invention claimed is:

1. A method of increasing cell-specific productivity of recombinant factor VIII (rFVIII) produced in an eukaryotic cell suspension comprising culturing the eucaryotic cell suspension in a culturing medium containing not more than 500 µM $CaCl_2$, at least a non-ionic detergent, and other nutrient components needed for the cells to grow and produce rFVIII while inducing mechanical shear stress to the eucaryotic cell suspension by adding a power density of at least 3 W/m$^3$.

2. The method of claim 1 wherein the power density is introduced into the cell culturing medium by a mechanical movement of the cell suspension.

3. The method of claim 2 wherein the mechanical movement of the cell suspension is performed by pumping the cell suspension through a tangential filter membrane.

4. The method of claim 2 wherein the mechanical movement of the cell suspension is performed of a rotating element.

5. The method of claim 1 wherein the rFVIII is a B-domain deleted rFVIII.

6. The method of claim 1 wherein the eukaryotic cells are HEK293 cells.

7. The method of claim 6 wherein the rFVIII molecule is produced in and associated with the HEK293 cells.

8. The method of claim 1 wherein the non-ionic detergents are selected from Pluronic-F68, Tween 20 and Tween 80.

9. The method of claim 1 wherein the non-ionic detergents have a concentration of 0.00001 wt % to 1 wt %.

10. The method according to claim 1 wherein cell aggregation is minimized by the not more than 500 μm $CaCl_2$ concentration in the culture medium and increasing $CaCl_2$ transport from the culture environment to the cells by the increasing shear.

11. The method of claim 1 wherein the mechanical movement of the cell suspension is initiated by an impeller equipped culturing container or a culturing container moving in gravity of earth inducing shear stress in said cell suspension or the shear stress in the cell suspension container is induced by pumping the cell suspension through a static mixer or a filter device.

12. The method of claim 1 wherein the power density added to the cell suspension to introduce shear stress is maximum 2000 $W/m^3$.

13. The method of claim 1 wherein the power density added to the cell suspension to introduce shear stress is from 3 $W/m^3$ to 2000 $W/m^3$.

14. The method of claim 3 wherein the tangential filter membrane is a hollow fiber membrane.

15. The method of claim 4 wherein the rotating element is a stirrer, propeller, or impeller.

16. The method of claim 1 wherein the non-ionic detergents have a concentration of 0.0001 wt % to 0.1 wt %.

17. The method of claim 1 wherein the non-ionic detergents have a concentration of 0.001 wt % to 0.01 wt %.

* * * * *